(12) United States Patent
Johnson, Jr. et al.

(10) Patent No.: US 8,171,808 B2
(45) Date of Patent: May 8, 2012

(54) MATERIAL SAMPLING DEVICE WITH ROTATABLE TUBE ASSEMBLY

(75) Inventors: George F. Johnson, Jr., Pikeville, KY (US); Viktor Andreevich Zhuravlov, Oleksandrivsk (UA)

(73) Assignee: Johnson Industries, Inc., Pikeville, KY (US)

( * ) Notice: Subject to any disclaimer, the term of this patent is extended or adjusted under 35 U.S.C. 154(b) by 454 days.

(21) Appl. No.: 12/433,281

(22) Filed: Apr. 30, 2009

(65) Prior Publication Data

US 2009/0272203 A1     Nov. 5, 2009

Related U.S. Application Data

(60) Provisional application No. 61/126,185, filed on May 2, 2008.

(51) Int. Cl.
   *G01N 1/20*       (2006.01)
(52) U.S. Cl. .................................................. 73/864.43
(58) Field of Classification Search ............... 73/864.43; 299/32, 39.9, 41.1
See application file for complete search history.

(56) References Cited

U.S. PATENT DOCUMENTS

| | | | | |
|---|---|---|---|---|
| 1,927,871 | A | | 9/1933 | Irwin et al. ............... 73/864.43 |
| 2,197,989 | A | | 4/1940 | Tyler et al. ...................... 175/91 |
| 3,217,546 | A | * | 11/1965 | Cordell et al. ............. 73/863.56 |
| 3,217,548 | A | * | 11/1965 | Cordell et al. ............. 73/863.57 |
| 3,447,381 | A | | 6/1969 | Clark et al. ................ 73/864.43 |
| 3,722,715 | A | | 3/1973 | Young ............................ 414/292 |
| 3,822,600 | A | | 7/1974 | Stonner et al. ............. 73/864.43 |
| 4,159,149 | A | * | 6/1979 | Castanoli et al. ............ 299/80.1 |
| 4,345,484 | A | | 8/1982 | Gould et al. ................ 73/864.43 |
| 4,750,571 | A | | 6/1988 | Geeting ........................... 175/57 |
| 5,211,062 | A | | 5/1993 | Moser ....................... 73/864.33 |
| 5,413,004 | A | | 5/1995 | Johnson, Jr. et al. ...... 73/863.41 |
| 6,193,053 | B1 | | 2/2001 | Gaalswyk ..................... 198/662 |
| 6,863,520 | B1 | | 3/2005 | Stiles ............................ 425/280 |
| 7,775,300 | B2 | * | 8/2010 | Krollmann ....................... 175/57 |

\* cited by examiner

*Primary Examiner* — Hezron E Williams
*Assistant Examiner* — Tamiko Bellamy
(74) *Attorney, Agent, or Firm* — Frost Brown Todd LLC

(57) ABSTRACT

A material sampling device comprises an auger, a first motor, and a rotatable tube assembly. The auger is configured to extract material from a container. The first motor is configured to rotate the auger. The rotatable tube assembly comprises an outer tube and a second motor. The outer tube is configured to allow the auger to rotate within the outer tube. The outer tube comprises an upper portion configured to remain stationary, and a lower portion configured to rotate. The second motor is configured to rotate the lower portion of the outer tube. In a second embodiment, a material sampling device comprises an auger, and a rotatable tube assembly. The rotatable tube assembly comprises an outer tube comprising an upper portion configured to remain stationary and a lower portion configured to rotate. The auger and the lower portion of the outer tube are configured to rotate simultaneously in opposite directions.

19 Claims, 12 Drawing Sheets

MATERIAL SAMPLING DEVICE WITH ROTATABLE TUBE ASSEMBLY

PRIORITY

This application claims priority from the disclosure of U.S. Provisional Patent Application Ser. No. 61/126,185, filed May 2, 2008, entitled "Rotating Tube on an Auger Sampling System," the disclosure of which is incorporated by reference herein in its entirety.

BACKGROUND

Material samples have been obtained in a variety of ways using a variety of devices. In particular, many different types of coal sampling devices have been used previously. One such exemplary coal sampling device is disclosed in U.S. Pat. No. 5,413,004, entitled "Method and Apparatus for Sampling Coal," issued May 9, 1995 to Johnson et al., the disclosure of which is incorporated by reference herein. While numerous material sampling devices have been made and used for extracting samples of various types of material, it is believed that no one prior to the inventors has made or used the invention described in the appended claims.

BRIEF DESCRIPTION OF THE DRAWINGS

While the specification concludes with claims that particularly point out and distinctly claim the invention, it is believed the present invention will be better understood from the following description taken in conjunction with the accompanying drawings, in which like reference numerals identify the same elements. The drawings and detailed description which follow are intended to be merely illustrative and are not intended to limit the scope of the invention as set forth in the appended claims.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 5:
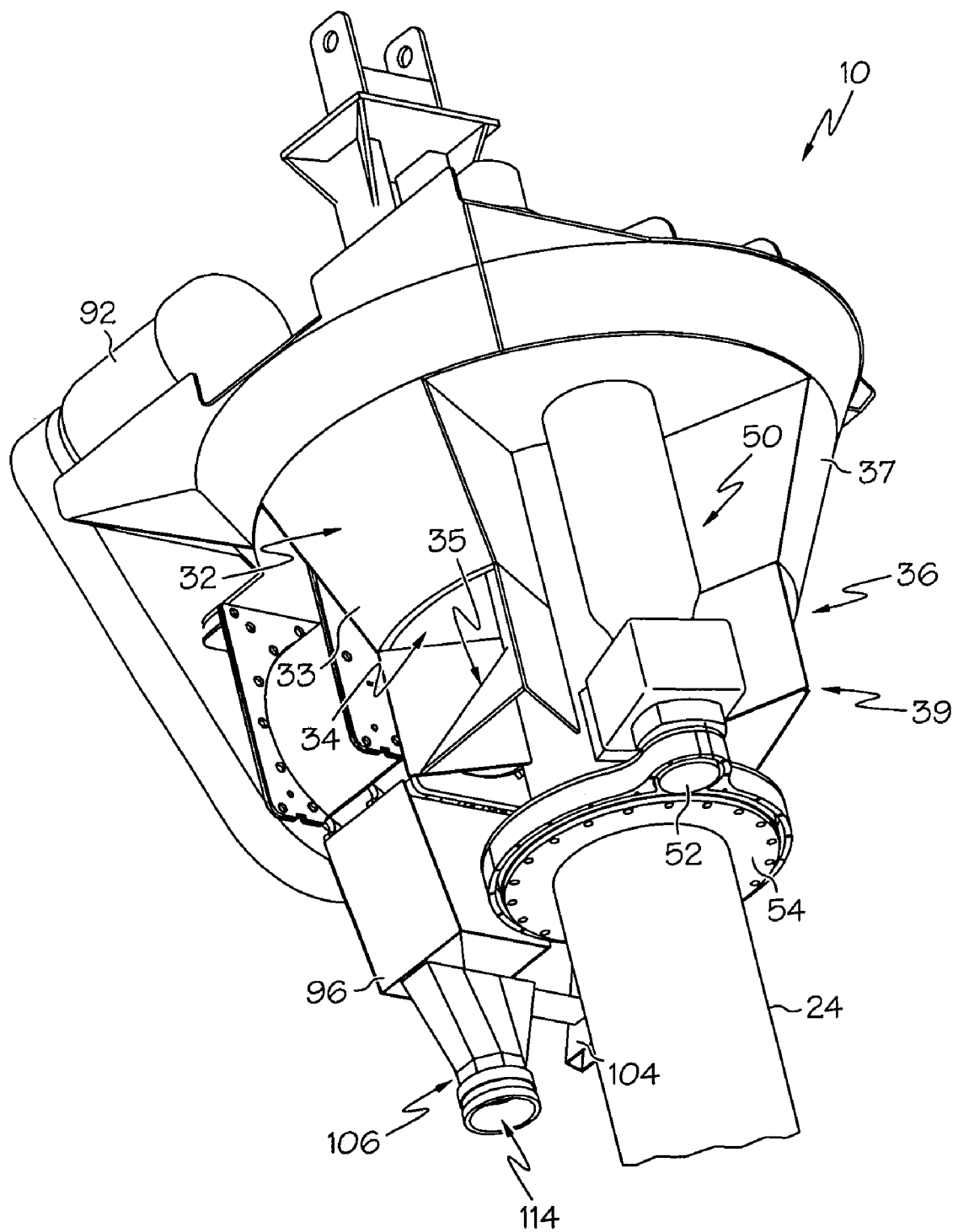
FIG. 5 depicts a detailed perspective view of the upper section of the device of FIG. 1.
Figure 6:
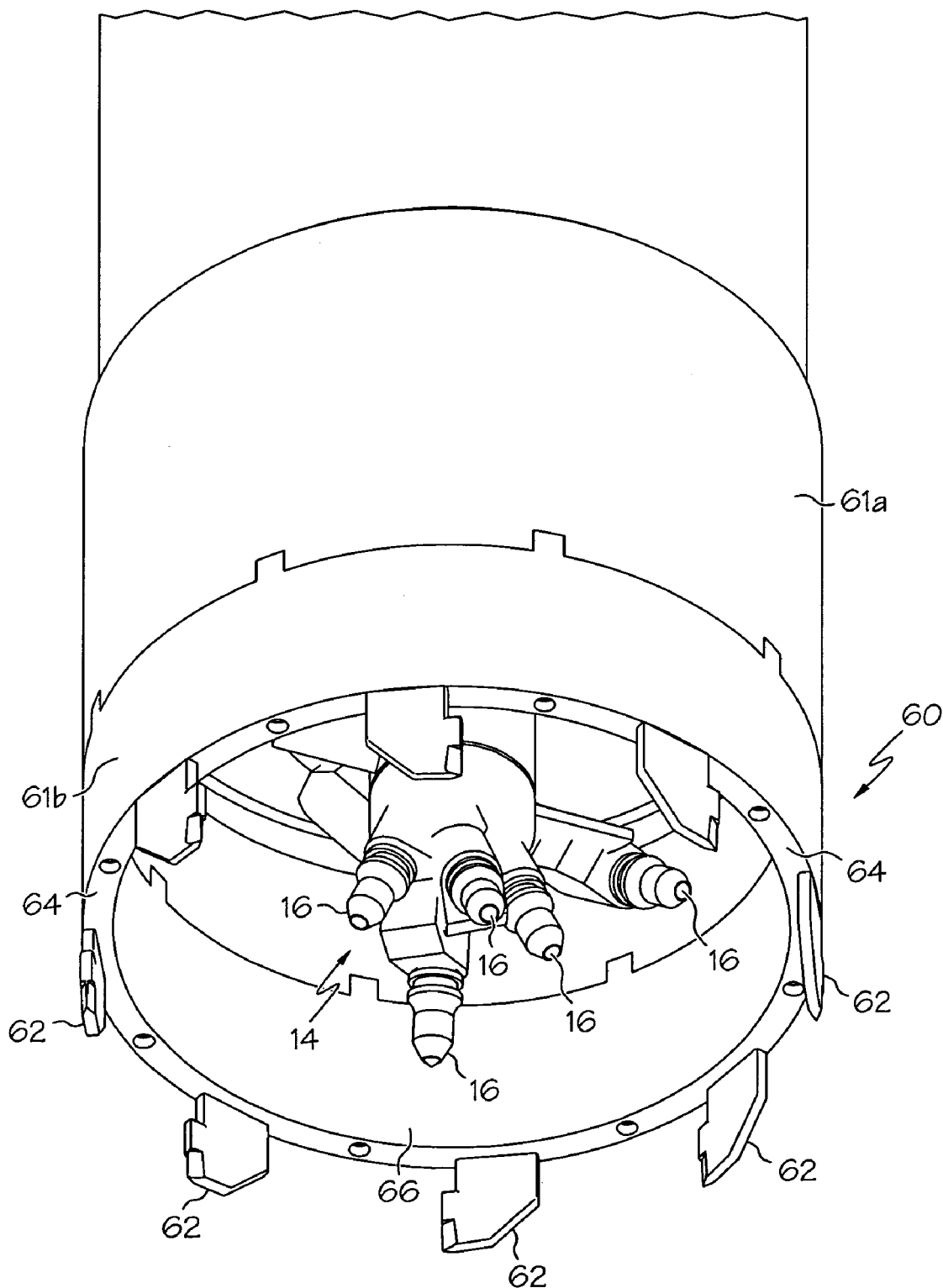
FIG. 6 depicts a detailed perspective view of the bottom section of the device of FIG. 1.

As shown in FIGS. 1-6 and 9-10 material sampling device 10 comprises a material extractor which turns inside an outer tube 20. In the illustrated example, the material extractor comprises a vertical blade auger 12, but it will be appreciated that other suitable conveying devices may be used. Material sampling device 10 may be used to obtain samples of any suitable material, including but not limited to coal, potash, iron ore, grain, gravel and other types of solid and granular materials having a consistency substantially similar to gravel or coal. In this version, auger 12 comprises an auger blade 15, which may also be referred to as auger flighting, an auger shaft 18, and an auger head 14 located at the bottom portion of auger 12. As shown in FIG. 6, auger head 14 includes teeth 16 configured to facilitate movement of auger 12 through the material to be sampled. Teeth 16 may comprise carbide or any other suitable material. Teeth 16 may comprise any suitable shape, number or configuration. Teeth 16 may be removably inserted into auger head 14, such that teeth 16 may be replaced, however, this is not required. Teeth 16 may be attached to auger head 14 using one or more fasteners, including but not limited to a snap ring and a bolt, a weld, or any other suitable method or device.

In the illustrated example, outer tube 20 is part of a rotatable tube assembly 120. As shown, rotatable tube assembly 120 comprises outer tube 20, a tube motor 50, a gear 52, a turntable bearing 54, and a bit head 60. As shown, outer tube 20 is substantially continuous along the entire length and around the entire circumference of outer tube 20, although this is not required. In this example, outer tube 20 comprises an upper portion 22 and a lower portion 24, and rotatable tube assembly 120 is configured to provide unidirectional or multidirectional rotation of lower portion 24 of outer tube 20. Upper portion 22 and lower portion 24 may comprise the same or different materials. By way of example only, upper portion 22 and lower portion 24 may comprise a metal, including but not limited to steel, or any other suitable rigid material. If multidirectional rotation of lower portion 24 of outer tube 20 is provided, sampling device 10 may further include a control (not shown) configured to allow a user to control the direction of rotation. In the illustrated version, the length of lower portion 24 is greater than upper portion 22, although any suitable dimensions may be used. In fact, in an alternate embodiment (not shown), upper portion 22 may be removed. In this alternate embodiment, turntable bearing 54 and tube motor 50 may be reconfigured and repositioned such that turntable bearing 54 is positioned adjacent to horizontal shelf 28 of separator subassembly 30 (described below), thereby eliminating upper portion 22.

Rotatable tube assembly 120 may be configured to allow lower portion 24 of outer tube 20 to be rotated independently of auger 12. As a result, lower portion 24 and auger 12 may be rotated simultaneously in the same direction or in opposite directions. Additionally, lower portion 24 may be rotated while auger 12 remains stationary, or auger 12 may be rotated while lower portion 24 remains stationary. As depicted, rotatable tube assembly 120 is configured to allow lower portion 24 to rotate, while upper portion 22 remains fixed and does not rotate. The individual components of rotatable tube assembly 120 and their relationships will be described in more detail below. Rotatable tube assembly 120 is shown in FIGS. 1-6 and 9-10 and is described below in conjunction with a material sampling device similar to the sampling device disclosed in U.S. Pat. No. 5,413,004, entitled "Method and Apparatus For Sampling Coal," issued to Johnson et al. on May 9, 1995. However, it will be appreciated by those skilled in the art that rotatable tube assembly 120 may be used in conjunction with other types of material sampling devices as well.

Figure 3:
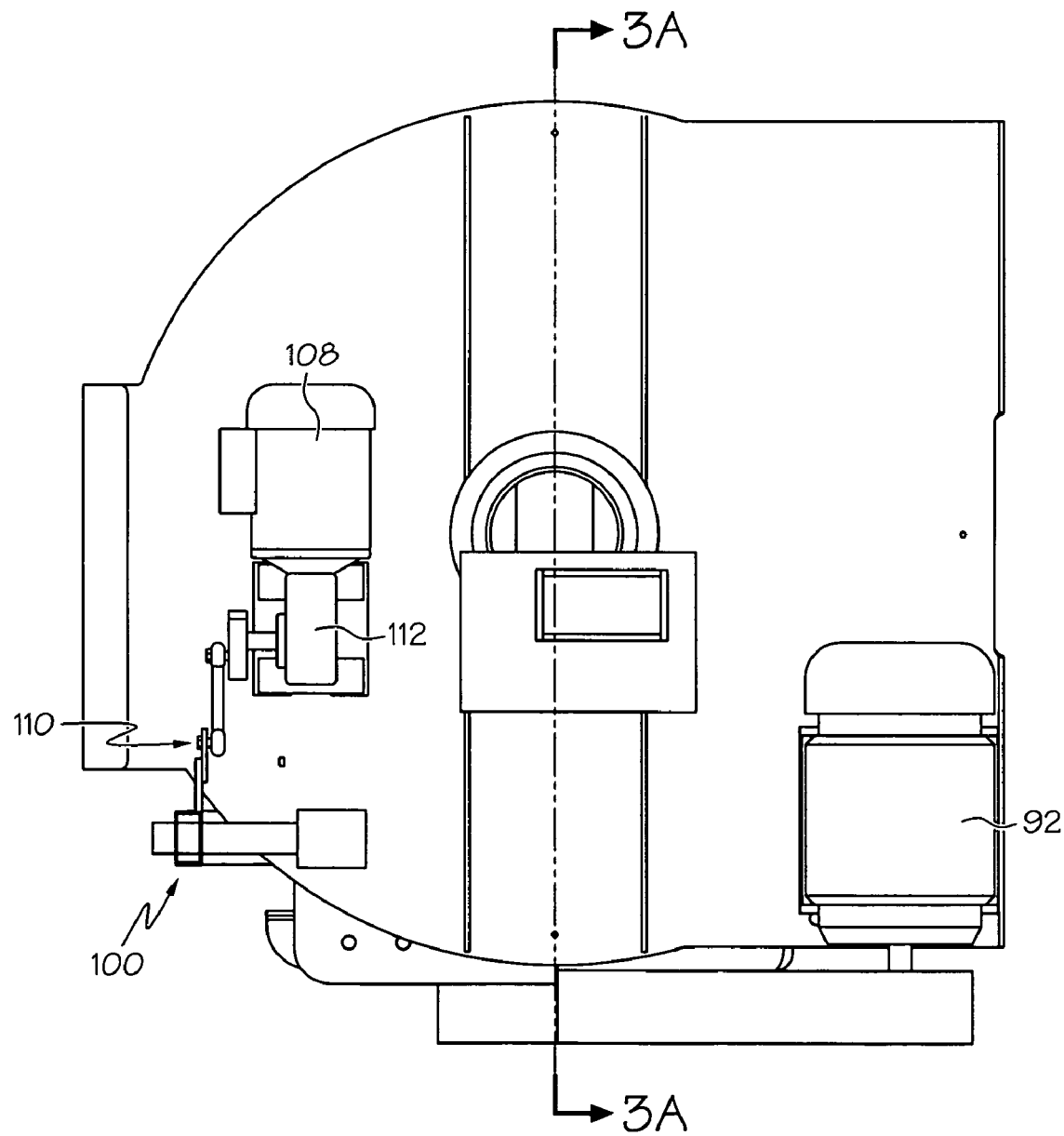
FIG. 3 depicts a top plan view of the device of FIG. 1.
Figure 3A:
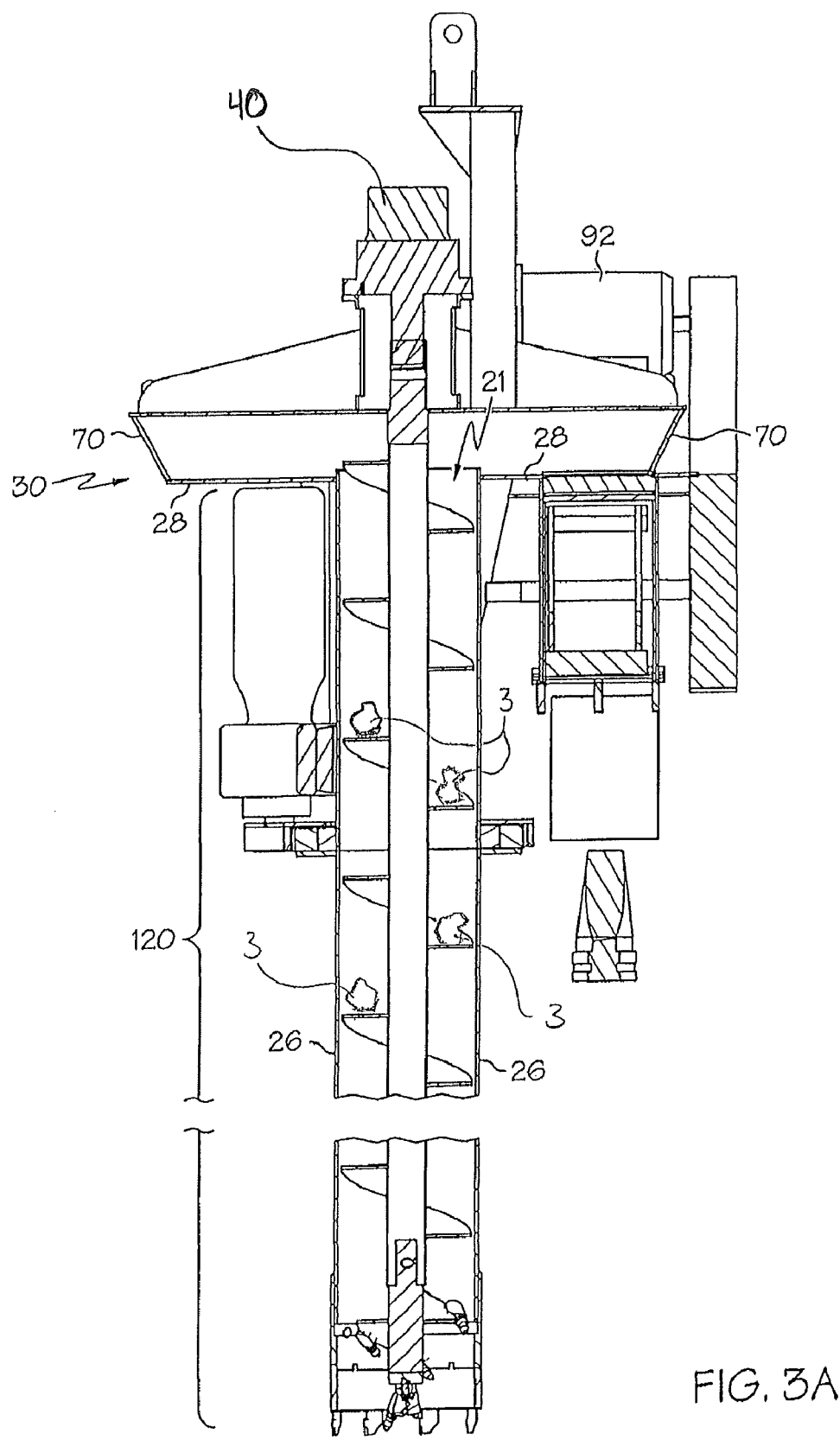
FIG. 3A depicts a cross-sectional, side view of the device of FIG. 1 taken along the line 3A-3A in FIG. 3.
Figure 4:
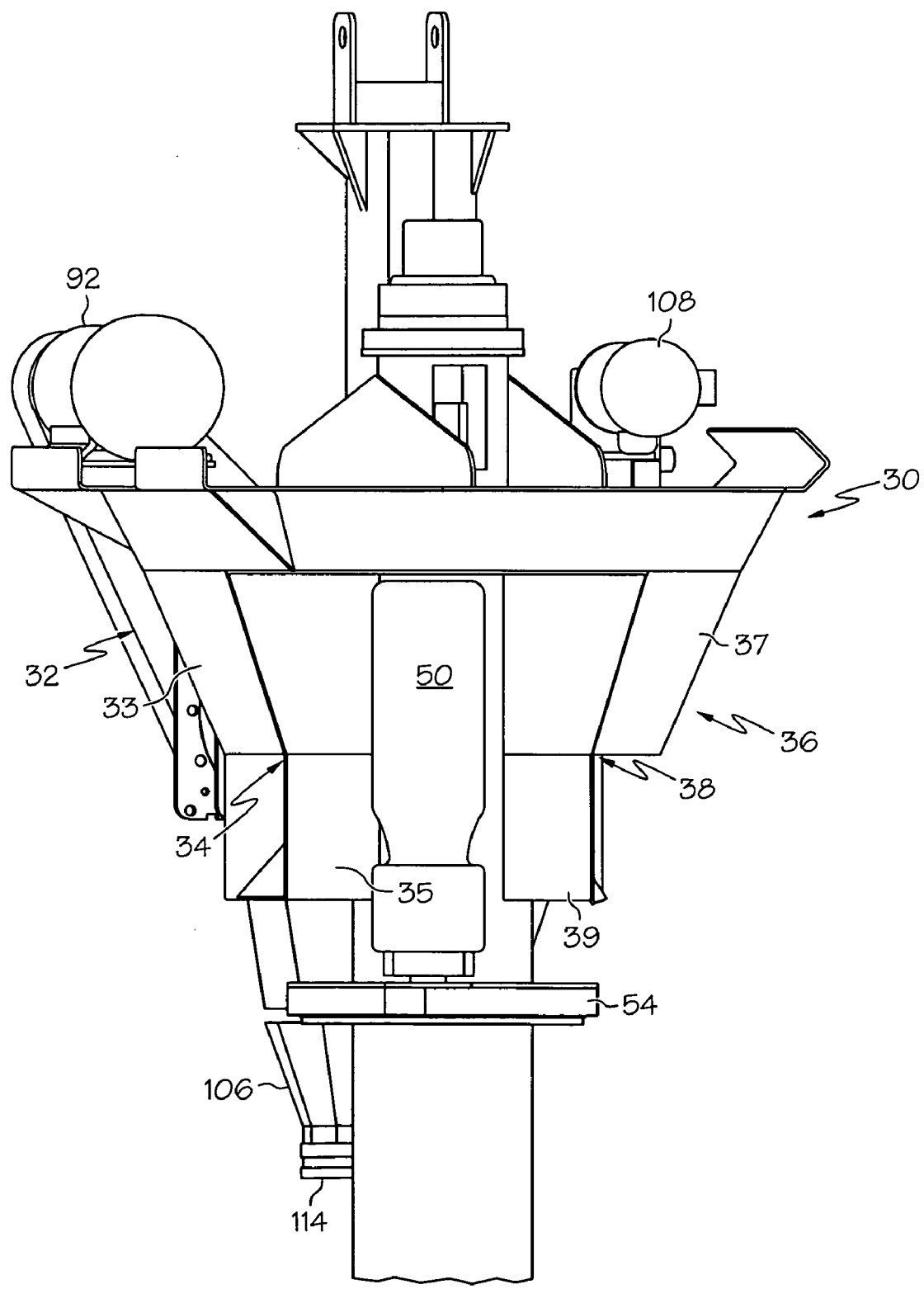
FIG. 4 depicts a side view of the upper section of the device of FIG. 1.

As shown, a funnel-shaped separator subassembly 30 is adjacent to the top edge of upper portion 22 of outer tube 20. In this version, auger blade ends in separator subassembly 30, however auger shaft 18 continues further up in the vertical direction to an auger drive coupling 42. In the illustrated example, auger shaft 18 is propelled by an auger motor 40. Auger motor 40 may be configured to provide unidirectional or multidirectional rotation of auger 12. If multidirectional rotation of auger 12 is provided, sampling device 10 may further include a control (not shown) configured to allow a user to control the direction of rotation. Auger motor 40 may comprise an electric motor, a hydraulic motor, an air motor, a combustion motor, or any other suitable type of motor or device. In one embodiment, auger motor 40 comprises a motor having 65 horsepower and configured to run at 1050 rpm. Of course, other suitable motors producing different amounts of horsepower and configured to run at different speeds may be used as well. As shown in FIG. 3, the output of auger motor 40 is connected to a gearbox 44, and the output of gearbox 44 is then connected to auger drive coupling 42. Gearbox 44 may comprise a planetary reduction gearbox or any other suitable device. In one embodiment, auger 12 is configured to rotate at a speed within a range from about 140 rpm to about 160 rpm, however this is not required.

In the illustrated version, lower portion 24 of outer tube 20 is rotatable, while upper portion 22 is configured to remain stationary. As shown, rotatable tube assembly 120 includes a tube motor 50 mounted adjacent to upper portion 22 and configured to rotate lower portion 24 of outer tube 20. Tube motor 50 may comprise an electric motor, a hydraulic motor, an air motor, a combustion motor, or any other suitable type of motor or device. In one embodiment tube motor 50 comprises a 380 volt, 50 Hz electric motor having 12.5 horsepower and configured to run at 271 rpm. Of course, other suitable motors producing different amounts of horsepower and configured to run at different speeds may be used as well, including but not limited to a 480 volt electric motor. In this example, tube motor 50 is in mechanical communication with a gear 52, such that tube motor 50 is configured to rotate gear 52. Gear 52 may comprise a 22-tooth gear or any other suitable gear or device. Gear 52 is in mechanical communication with a turntable bearing 54, which is itself in communication with lower portion 24. As shown, turntable bearing 54 is positioned circumferentially around lower portion 24. Turntable bearing 54 may comprise a circumferential gear configured to mesh with gear 52. In one embodiment, turntable bearing 54 comprises 101 teeth around its circumference. Accordingly, when tube motor 50 is activated to rotate, such rotation will cause gear 52, turntable bearing 54, and lower portion 24 to rotate. In other words, rotation of tube motor 50 will be communicated to lower portion 24 via gear 52 and turntable bearing 54. It will be appreciated that other suitable structures may be used instead of or in conjunction with a turntable bearing, including but not limited to a plurality of rollers, and a roller bearing. In one embodiment, lower portion 24 is configured to rotate at a speed of about 60 rpm, however this is not required. Of course, these components are merely illustrative, and any other suitable components, configurations, or techniques may be used to cause rotation of lower portion 24.

As shown and described above, rotation of lower portion 24 is powered independently of auger 12. Thus, lower portion 24 may be rotated simultaneously with auger 12 in the same direction or the two components may be rotated simultaneously in opposite directions. In addition to being configured to provide independent control of the direction of rotation for lower portion 24 and auger 12, the use of individual power sources for these two components may also provide the ability to independently vary the speed of rotation for each component. For instance, in one embodiment, tube motor 50 may be configured to rotate lower portion 24 at a speed of about 60 rpm, while auger motor 40 may be configured to simultaneously rotate auger 12 at a speed within a range from about 140 rpm to about 160 rpm. Of course, lower portion 24 and auger 12 may be rotated at substantially equivalent or any other suitable rotational speeds. Material sampling device 10 may also be configured to allow either lower portion 24 or auger 12 to rotate while the other component remains stationary.

In the illustrated version, outer tube 20 further comprises a bit head 60 positioned on the bottom end of lower portion 24. As shown, bit head 60 comprises an upper ring 61a and a lower ring 61b. Upper ring 61a and lower ring 61b may be releasably or fixedly attached to each other using any suitable device or method. Upper ring 61a may be integral with lower portion 24, although this is not required. In alternate embodiments, bit head 60 may comprise a single-piece construction or bit head 60 may comprise three or more individual components. Upper ring 61a and lower ring 61b may each comprise the same material, although this is not required. Bit head 60 may comprise the same or different material than one or both of upper portion 22 and lower portion 24. In one embodiment, bit head 60 comprises a material that is harder than the material comprising upper portion 22 and/or lower portion 24. By way of example only, bit head 60 may comprise metal, including but not limited to steel, or any other suitable material. Bit head 60 may be a discrete component permanently or releasably attached to lower portion 24 via any suitable attachment means, including but not limited to welding, fasteners, a bit ring, and a flange. Alternatively, bit head 60 may comprise an integral portion of outer tube 20. As shown in FIG. 6, bit head 60 comprises a plurality of teeth 62 positioned along the circumference of the lower edge 64 of bit head 60. Teeth 62 are configured to facilitate movement of the material sampling device 10 through the material by cutting through obstructions in the material. Teeth 62 may comprise carbide or any other suitable material. Teeth 62 may be removably inserted along the circumference of the lower edge 64 of bit head 60, such that teeth 62 may be replaced, however, this is not required. In such an embodiment, teeth 62 may be inserted into an opening (not shown) and comprise a snap ring that expands upon insertion into the opening, thereby releasably attaching teeth 62 to bit head 60. Alternatively, teeth 62 may be attached to bit head 60 using one or more fasteners, including but not limited to a bolt, a weld, or any other suitable method or device. Teeth 62 may comprise any suitable shape and dimensions, and bit head 60 may comprise any suitable number and configuration of teeth 62. In the illustrated embodiment bit head 60 comprises a thickness that is greater than the thickness of lower portion 24. The increased thickness of bit head 60 may increase the strength of outer tube 20. In an alternate embodiment (not shown), bit head 60 may comprise a thickness that is substantially equivalent to or less than the thickness of lower portion 24. In such an embodiment, a reduction in the thickness of bit head 60 may be possible based on the use of a material that provides increased hardness and durability.

Figure 7:
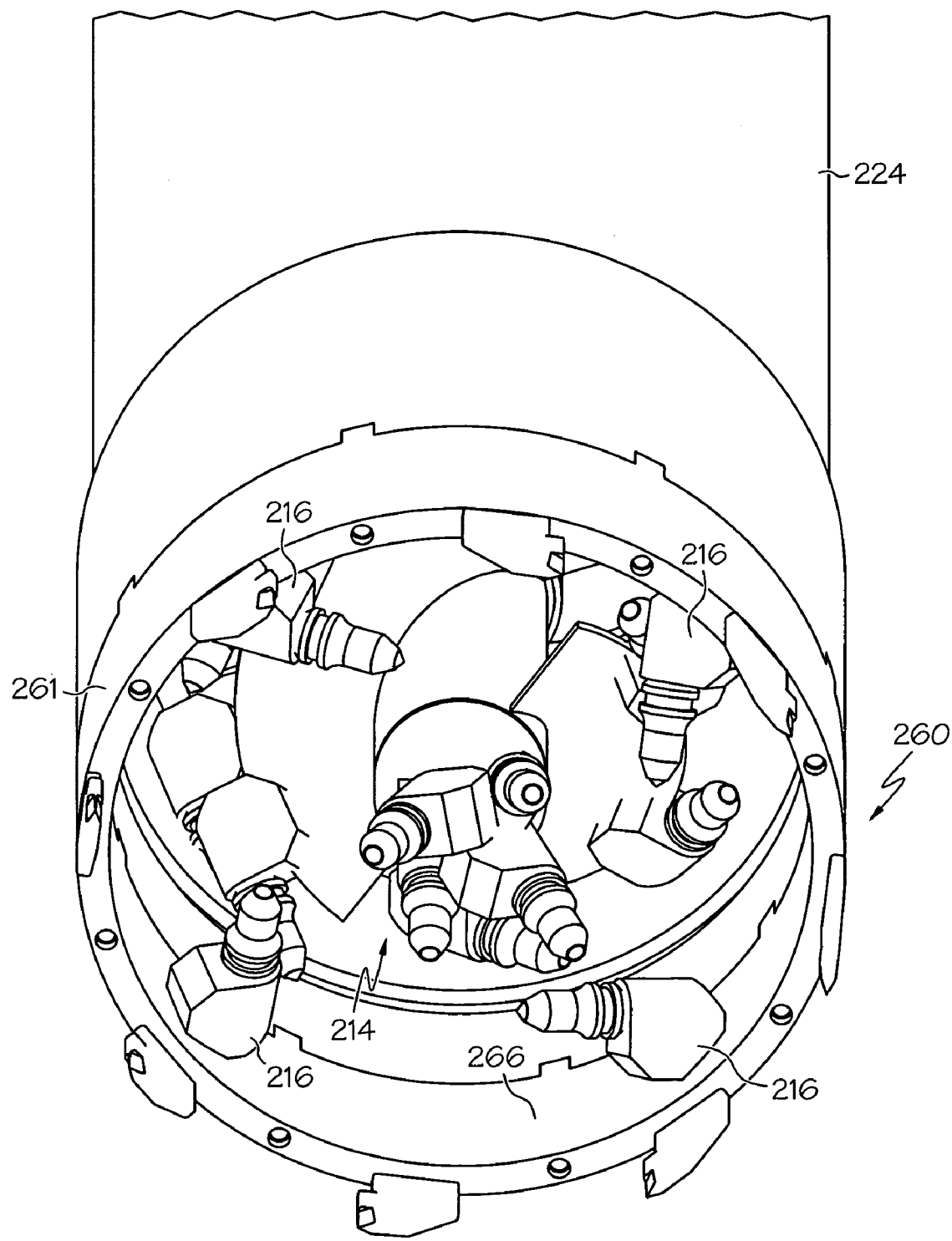
FIG. 7 depicts a detailed perspective view of an alternate embodiment of a material sampling device with an alternate bit head.
Figure 8A:
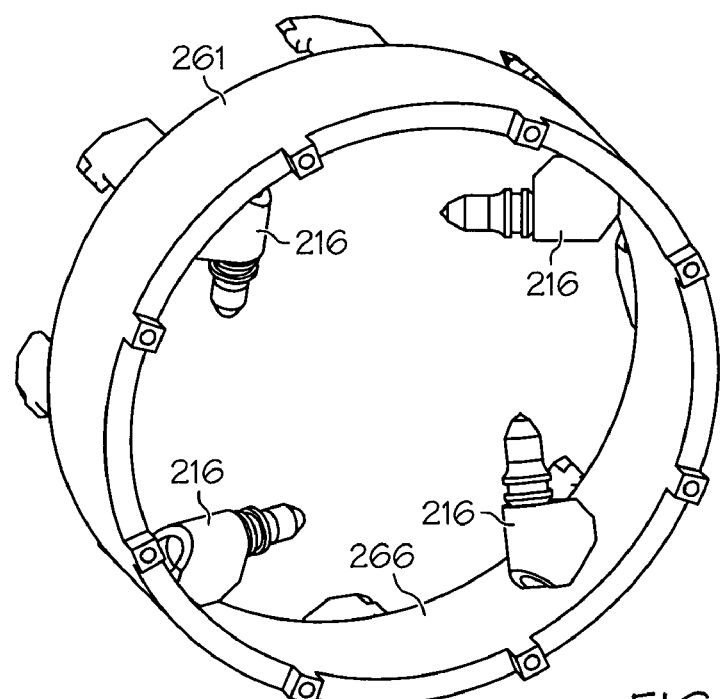
FIG. 8A depicts a perspective view of a lower ring of the bit head of FIG. 7.
Figure 8B:
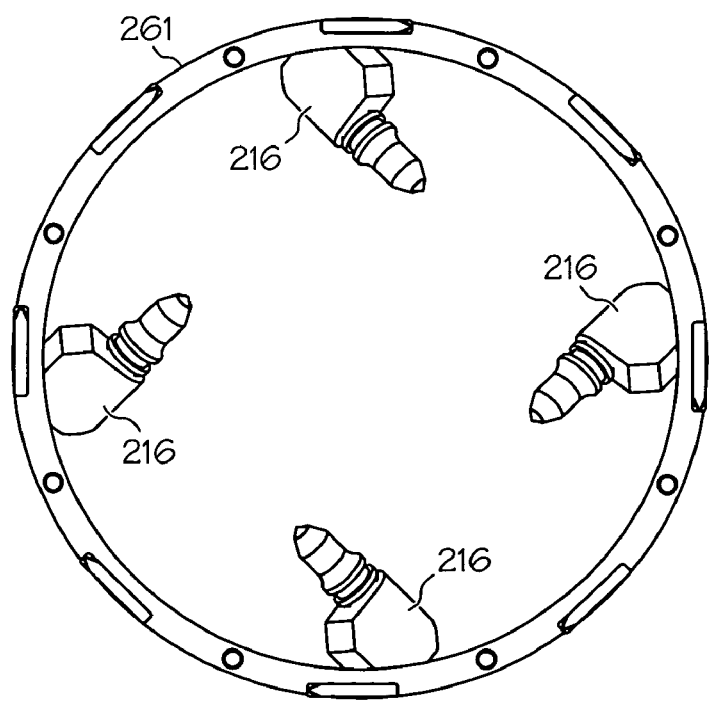
FIG. 8B depicts a front view of the lower ring of the bit head of FIG. 7.

In an alternate embodiment, bit head 60 may comprise one or more features positioned on the interior surface 66 of bit head 60 configured to produce an additional crushing action and facilitate movement of material sampling device 10 through the material. These features may be attached to or integral with bit head 60 and may include, but are not limited to teeth, spirals, projections, protuberances, or any other suitable features. Of course, these internal features are not required. By way of example only, FIGS. 7, 8A and 8B depict an embodiment comprising a bit head 260 positioned at the lower end of a lower portion 224, wherein bit head 260 surrounds an auger 214, similar to auger 14 described above. As shown, bit head 260 comprises a plurality of teeth 216 positioned circumferentially along the interior surface 266 of lower ring 261. In the illustrated embodiment teeth 216 are similar to teeth 16 described above. Of course, teeth 216 may comprise any suitable shape, number or configuration. Teeth 16 may comprise carbide or any other suitable material. Teeth 16 may be removably inserted into lower ring 261, such that teeth 16 may be replaced, however, this is not required. Teeth 16 may be attached to lower ring 261 using one or more fasteners, including but not limited to a snap ring and a bolt, a weld, or any other suitable method or device.

While the operation of material sampling device 10 will be described below in conjunction with obtaining samples of coal in a container, it will be appreciated that material sampling device 10 may be used to obtain samples of any suitable solid or granular material. The material may be housed in any suitable container, arranged in a free-standing mound or pile, located within the ground or a rock formation, or in any other suitable location. During operation, material sampling device 10 may be lowered into a container 7 of coal, such as a typical loaded coal truck. Material sampling device 10 may be used to extract samples from coal contained in railroad hopper cars or barges, or any other type of container which holds coal. It will be understood that, as used herein, the term "coal" represents coal and its impurities, which may include a large quantity of rock material in a "coal" sample.

During use, material sampling device 10 is lowered into the container holding the coal until the auger head 14 reaches the top portion of the coal in that container. In the illustrated version, as auger 12 turns, coal is extracted from the container and the coal moves up outer tube 20 in the direction of arrows 5. Material sampling device 10 may be lowered throughout the majority of the vertical portion of the coal held in the container. As material sampling device 10 is lowered through the material, it may encounter obstructions contained within the material. Lower portion 24 of outer tube 20 may be rotated in order to facilitate movement of material sampling device 10 through the material and any obstructions. Simultaneous rotation of lower portion 24 and auger 12, particularly when lower portion 24 and auger 12 are simultaneously rotated in opposite directions, may create a crushing and conveying action that may help material sampling device 10 cut through the material and any obstructions therein, while also helping prevent formation of a plug of material that could block outer tube 20. By way of example only, lower portion 24 may be rotated in a clockwise direction while auger 12 is rotated in a counter-clockwise direction simultaneously. Of course, the orientations of the rotation may be reversed, or lower portion 24 and auger 12 may be rotated in the same direction. Alternatively, only one of auger 12 and lower portion 24 may be rotated at a time. In this way, a complete core sample may be extracted from the coal held by the container.

Figure 1:
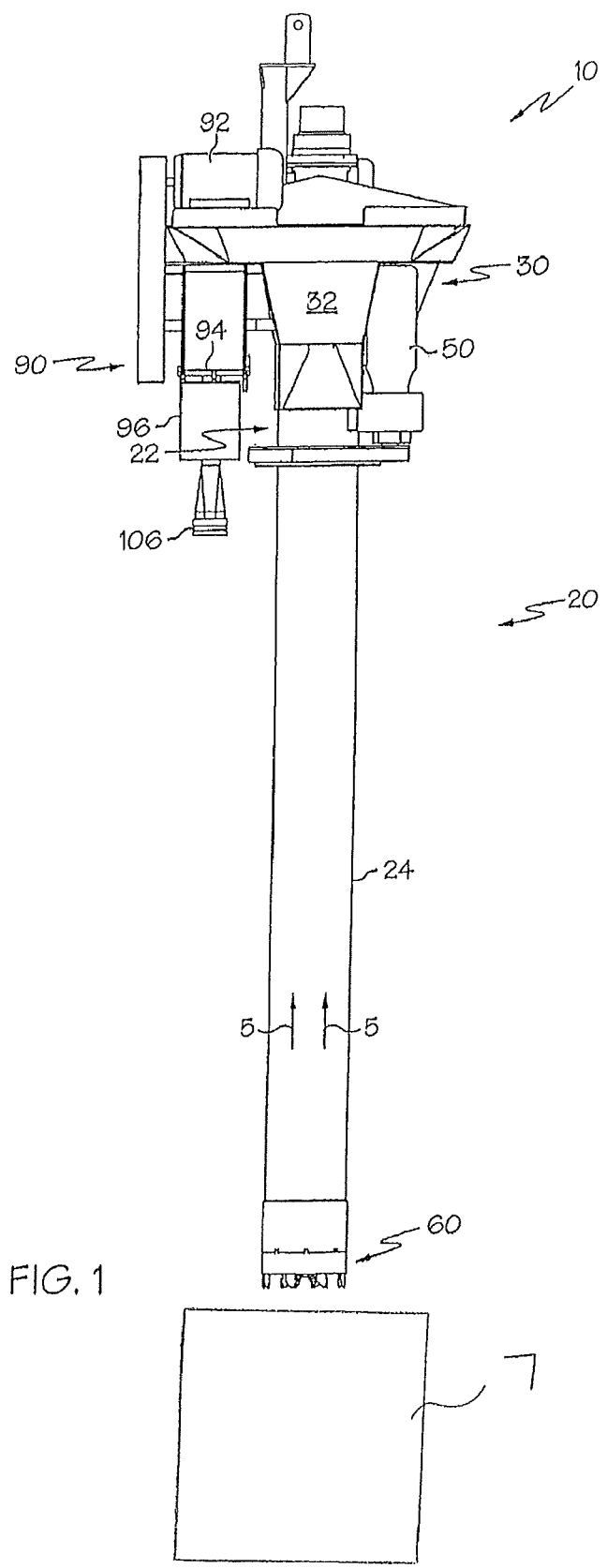
FIG. 1 depicts a side view of a material sampling device.
Figure 1A:
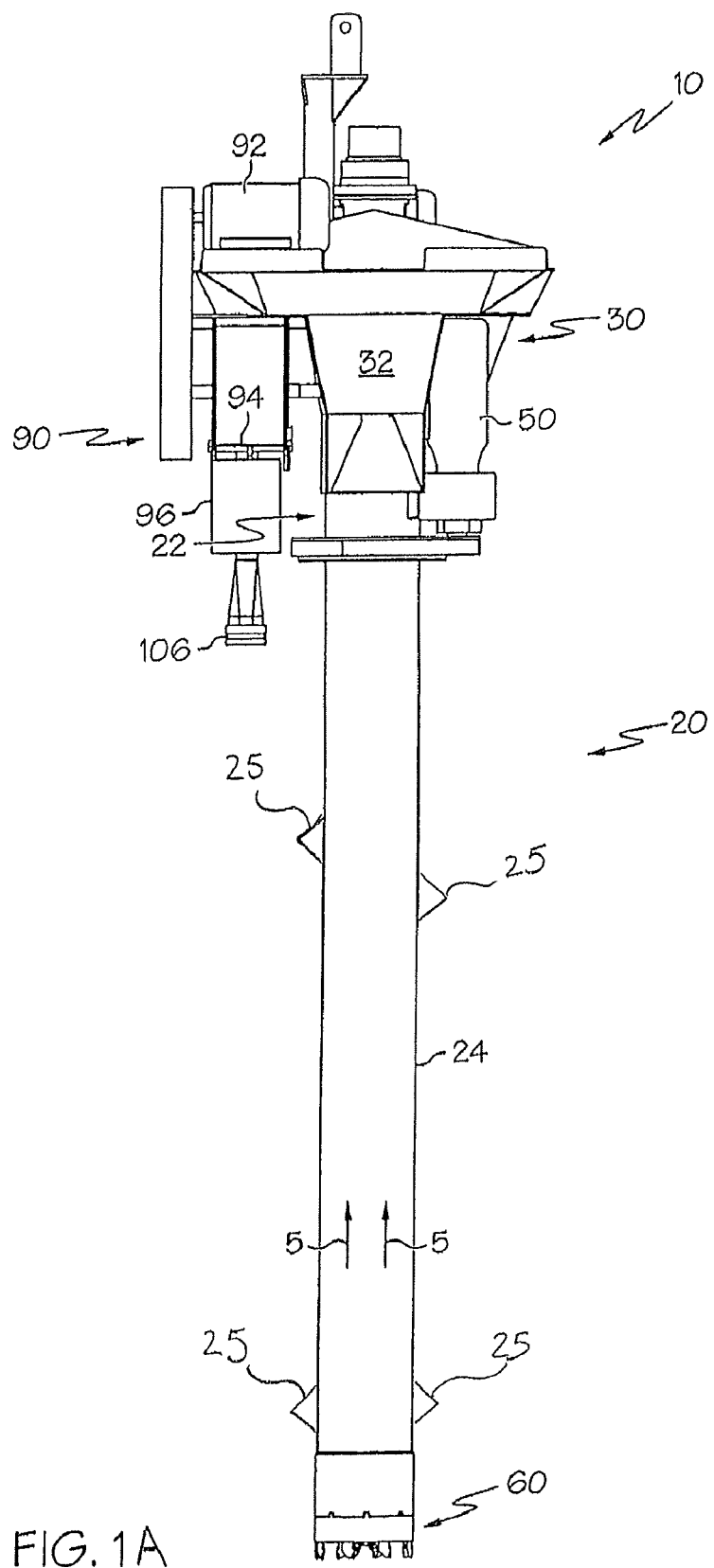
FIG. 1A depicts an alternate embodiment of the device of FIG. 1 that includes external features on the outer wall of the outer tube.
Figure 2:
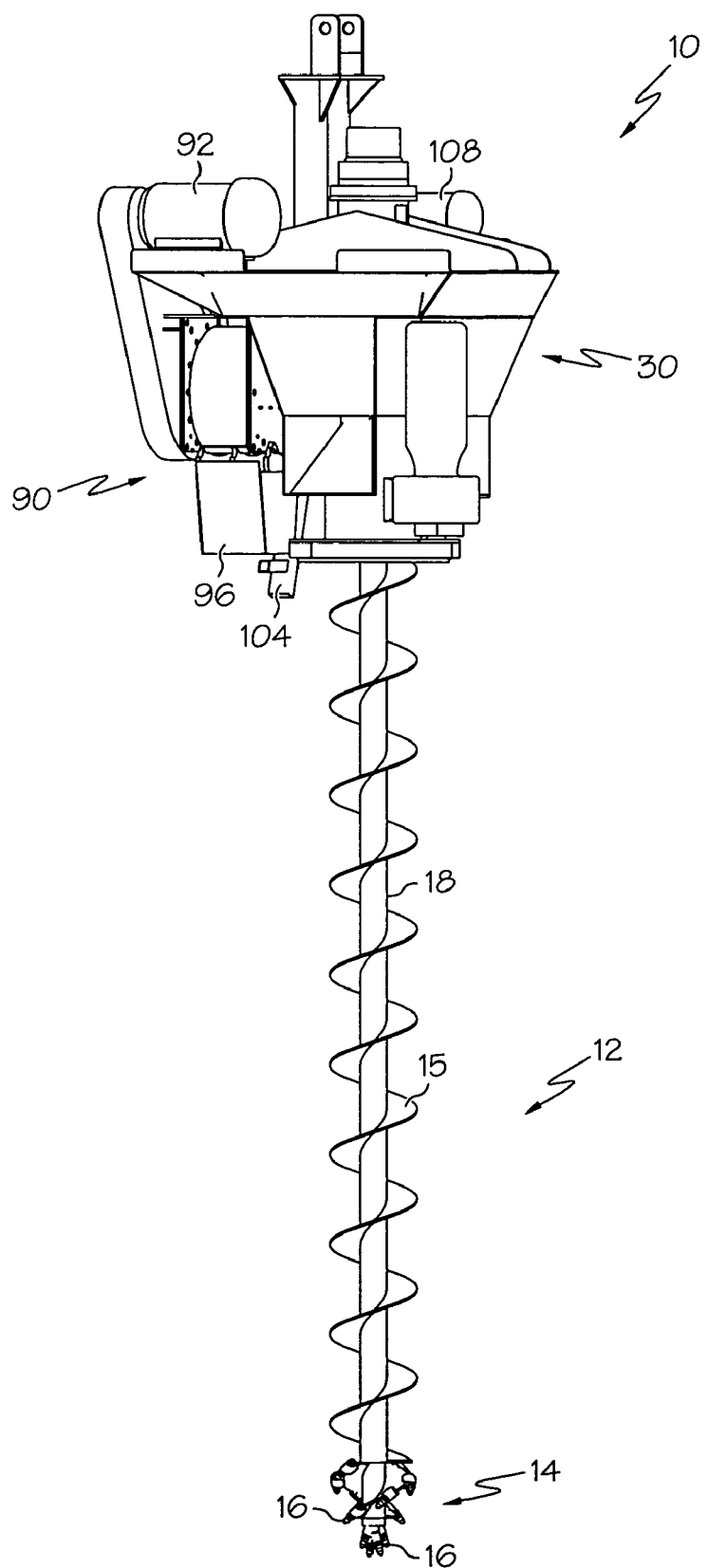
FIG. 2 depicts a side view of the device of FIG. 1 with the lower portion of the outer tube removed to reveal the auger.

As shown in FIG. 1, as coal 3 is extracted upward, along the direction indicated by arrows 5, it is contained by the outer wall 26 of outer tube 20. Rotating lower portion 24 in the opposite direction of auger 12 may facilitate movement of the material up outer tube 20 by providing frictional forces between auger 12 and lower portion 24. As shown, outer wall 26, along the entire length of upper portion 22 and lower portion 24, including bit head 60, comprises a substantially smooth outer surface. In an alternate embodiment, shown in FIG. 1A outer wall 26 may comprise external features 25, such as teeth, spirals, projections, protuberances, or any other suitable external feature attached to or integral with outer wall 26. The external features 25 may be positioned along bit head 60, along a limited section of lower portion 24, or along substantially the entire length of lower portion 24. The external features 25 may facilitate movement of material sampling device through the material. Of course, these external features are not required.

Figure 10:
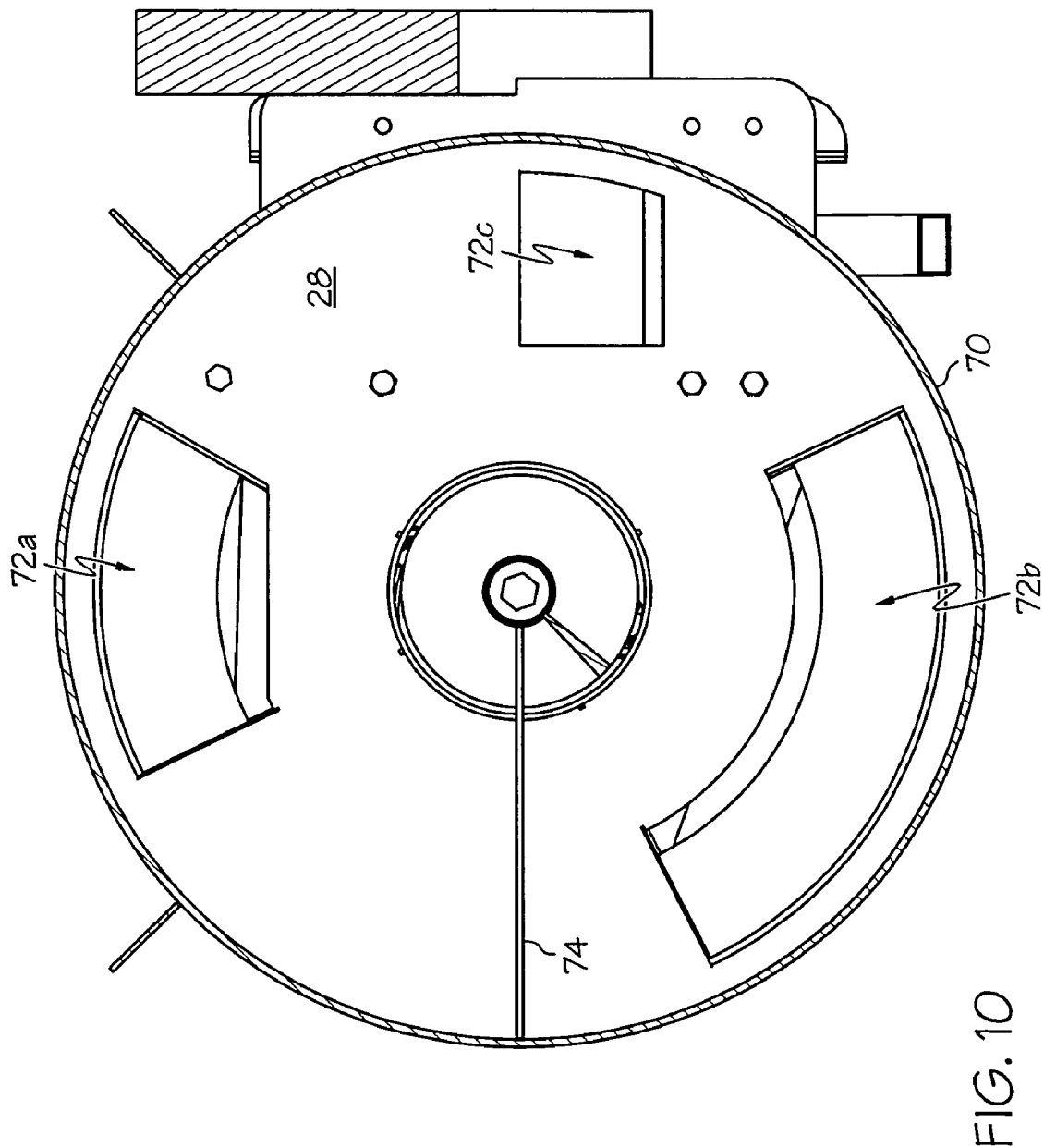
FIG. 10 depicts a partially cut a way top plan view of the coal sampling device of FIG. 1 with the top portion of the separator subassembly removed to reveal the interior components of the separator subassembly.

In the illustrated embodiment, near the top of auger blade 15, the upper edge of outer wall 26 is adjacent to a horizontal shelf 28 that extends outward at approximately a 90 degree angle from outer wall 12 to form a circular horizontal member. The open upper end 21 of outer tube 20 and horizontal shelf 28 may provide an outlet for the extracted coal moving up outer tube 20. Surrounding this portion of material sampling device 10 is a tapered conical wall 70 of separator subassembly 30. As shown in FIG. 10, there are three windows 72a, 72b, 72c formed in horizontal shelf 28. Pieces of coal may be conveyed upward via auger 12, urged through open upper end 21, onto horizontal shelf 28, and, subsequently, passed through one of windows 72a, 72b, 72c. While the illustrated version comprises three windows, it will be appreciated by those skilled in the art that any suitable number of windows in any suitable configuration, size and shape may be utilized.

As shown in the figures, separator subassembly 30 further comprises a first outlet shaft 32 and a second outlet shaft 36. In this example, window 72a opens into first outlet shaft 32 and window 72b opens into second outlet shaft 36. First outlet shaft 32 comprises a funnel section 33 configured to guide pieces of coal that fall through window 72a towards outlet opening 34 and discharge chute 35. Discharge chute 35 may be configured to direct pieces of coal away from outer tube 20 as the pieces of coal exit separator subassembly 30. Similarly, in the illustrated version, second outlet shaft comprises a funnel section 37 configured to guide pieces of coal that fall through window 72b towards outlet opening 38 and discharge chute 39. Discharge chute 39 may be configured to direct pieces of coal away from outer tube 20 as the pieces of coal exit separator subassembly 30.

As shown in FIG. 10, a rotating arm 74 is attached to auger shaft 18, so that when auger motor 40 turns, auger 12 and rotating arm 74 turn at the same rate. In this version, a spreader bar (not shown) is attached to the outer diameter portion of rotating arm 74. Spreader bar may comprise a piece of substantially flexible material, such as rubber or any other suitable material. As auger 12 turns, uncrushed pieces of coal which have traveled up outer tube 20 are pushed onto shelf 28. Such coal pieces may not necessarily forced off of the shelf 28 immediately, however, when the spreader bar comes into contact with such pieces of coal, it may tend to push those pieces of coal off shelf 28 and through one of windows 72a, 72b, 72c. The coal pieces that fall through window 72a may then fall via gravity through outlet shaft 32 and be guided by funnel section 33 until they fall through outlet opening 34 and out of separator subassembly 30 via discharge chute 35. Similarly, the coal pieces that fall through window 72b may then fall via gravity through outlet shaft 36 and be guided by funnel section 37 until they fall through outlet opening 38 and out of separator subassembly 30 via discharge chute 39. In this manner windows 72a, 72b, first outlet shaft 32, and second outlet shaft 36 act as discharge or return outlets to guide extracted coal back into its original container, if desired. Alternatively, such unused pieces of coal may be captured, transferred to another location via some type of conveying means, such as a hose, conveyor chute, slide, or any other suitable method or device, and retained at the new location.

In the illustrated version, window 72c opens into a crusher 90 such that the spreader bar (not shown) may push pieces of coal off horizontal shelf 28 through window 72c, thereby falling into the top portion of crusher 90. As shown, crusher 90 is powered by an a crusher motor 92 which is positioned on the upper portion of material sampling device 10. Crusher motor 92 may comprise an electric motor, a hydraulic motor, an air motor, a combustion motor, or any other suitable type of motor or device. The output shaft of crusher motor 92 may be connected to a first pulley configured to drive a second pulley via a drive belt. In an alternate version (not shown), crusher motor 92 may be directly coupled to the crusher shaft of crusher 90, thereby eliminating the belt and pulley structure shown in the figures and described above. In one embodiment, crusher motor 92 comprises a 380 volt electric motor having 10 horsepower and configured to run at 1500 rpm, although any suitable size motor may be used, including but not limited to a 480 volt electric motor. Crusher 90 may comprise any suitable standard coal crushing unit. By way of example only, crusher 90 may comprise a crushing unit such as the one describe in U.S. Pat. No. 7,360,725 issued to Johnson et al. on Apr. 22, 2008, although this is not required.

In this example, the coal pieces that enter crusher 90 are continuously crushed into smaller particles until they are small enough to fit through holes in the bottom floor 94 of crusher 90. The size of the holes in bottom floor 94 may be ⅜ inch (or 10 mm) in diameter, so that coal must be crushed to pebble-sized pieces smaller than ⅜ inch (about 10 mm) in diameter before it can exit crusher 90 through bottom floor 94. Of course, the holes in bottom floor 94 may be any suitable shape or size. In the illustrated version, crusher 90 further comprises a crusher chute 96 positioned below bottom floor 94 and configured to guide the crushed coal back into the container or into sampler subassembly 100.

Figure 9:
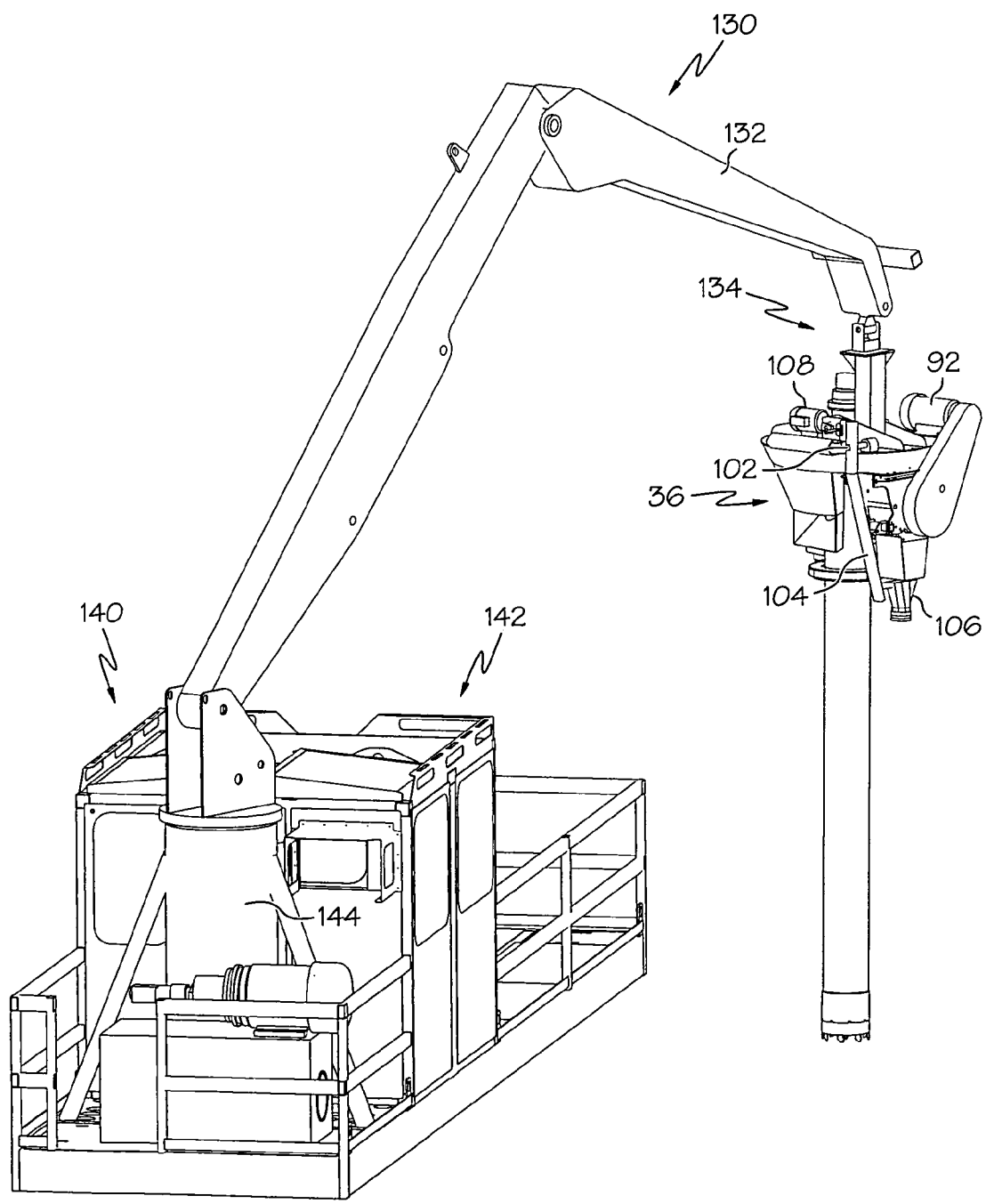
FIG. 9 depicts a perspective view of a trailer assembly that includes a hydraulic lift having a boom that supports the device of FIG. 1.

As shown, the crushed coal merely falls through crusher chute 96 and back to the container, via the holes in the bottom floor 94, unless captured by sampler subassembly 100. In this embodiment, sampler subassembly 100 comprises a pivot 102, a pivotable elongated arm 104, and a sample collecting receptacle 106. Sample receptacle 106 may be movable about pivot 102 such that sample receptacle 106 may travel across the opening of crusher chute 96 between rest positions on opposite sides of crusher chute 96. Sampler subassembly 100 may be configured such that when sample receptacle 106 is located in one of the two rest positions, sample receptacle 106 does not receive any of the crushed coal pieces as they fall through crusher chute 96 and return to the container. Sample receptacle 106 may only receive crushed coal particles as sample receptacle 106 travels between rest positions, or in other words, while sample receptacle 106 is in a moving, mid-travel position (as shown in FIGS. 1, 5, and 9). In the illustrated embodiment, a swing arm motor 108 provides the drive for moving sampler subassembly 100 via linkage 110. Swing arm motor 108 may comprise an electric motor, a hydraulic motor, an air motor, a combustion motor, or any other suitable type of motor or device. In one embodiment, swing arm motor 108 comprises a 220v electric motor having 0.5 horsepower and configured to run at 1425 rpm, although any suitable size motor may be used. As shown, swing arm motor 108 drives into a speed reducing gearbox 112, which may have a 40:1 gear ratio. It will be appreciated, that any other suitable device may provide the drive for moving sampler subassembly 100, including, but not limited to a linear actuator.

In one embodiment, during the operation of material sampling device 10, as it extracts coal from a fully loaded truck, for example, a substantial amount of coal will be augered up outer tube 20 and captured into the separator subassembly 30. If all of this coal needed to be crushed in the short time period that is typically required by a coal production facility, then a much larger sampler typically requiring a larger horsepower crusher would be required. However, material sampling device 10 only crushes a fraction of the coal extracted from the truck in the illustrated embodiment. By way of example only, about 16.67% of the coal augered up outer tube 20 and captured into separator subassembly 30 may fall into crusher 90, while the remaining approximately 83.33% of the coal may return to the container or pile from which it was extracted. Therefore, crusher 90 may only need to crush a smaller amount of coal during that same time period, and a much smaller crusher may be used, such as one requiring 10 horsepower or less in size.

The depicted embodiment may produce a crushed sample of coal that is still much greater than is needed for laboratory analysis. Therefore, sampler subassembly 100 may be configured to only capture a smaller final sample of the crushed coal out of the larger amount of crushed coal which is falling through the holes in crusher floor 94. In one embodiment, sampler subassembly 100 may be configured to produce constant motion of sample receptacle 106. In other words, sample receptacle 106 may be configured to constantly sweep back and forth across crusher floor 94 between rest positions. In such an embodiment, the constant motion of sample receptacle 106 may result in sample receptacle 106 capturing about ⅓ of the coal crushed by crusher 90 and falling through the holes in crusher floor 94. In an alternate embodiment, sampler subassembly 100 may incorporate a timer or some other suitable device configured to vary the sweeping frequency of sample receptacle 106. The amount of time sample receptacle 106 spends in one of the rest positions may be varied. The amount of coal captured by sample receptacle 106 may be varied by varying the amount of time sample receptacle 106 spends in one of the rest position, such that increasing the amount of time sample receptacle 106 spends in one of the rest positions may decrease the amount of coal captured by sample receptacle 106.

In one mode of operation, sampler subassembly 100 is configured to keep the sample receptacle 106 in one of the rest positions for approximately three seconds at a time, then to sweep or "cut" underneath crusher floor 94, while moving sample receptacle 106 through its mid-travel position, within a time interval of about one second or less sweep time. In this way, the coal particles may be sampled throughout the operation of the auger such that somewhat random samples of coal may be accumulated from start to finish. This may ensure that a representative sample of the core drilled by auger 12 will be accumulated for laboratory analysis. Sample receptacle 106 may be configured to make a minimum of six "secondary" cuts per each penetration of auger 12 into the coal container. In this way, the proper amount of crushed coal may be accumulated by sample receptacle 106 at the end of the core extraction procedure.

In addition to the somewhat random sampling of sampler subassembly 100, the overall design of spreader bar (not shown) and windows 72a, 72b, 72c may prevent an accidental or intentional bias by a system operator as to which coal pieces fall into crusher 90. A fairly representative sample of the overall core extracted by material sampling device 10 may be accumulated in sample receptacle 106.

In the illustrated version, sample receptacle 106 comprises discharge opening 114 located at the bottom of sample receptacle 106. In one embodiment a hose (not shown) may be connected to discharge opening 114. The hose may be connected to a receptacle bag (not shown) or some other container inside the operator's cab 142 or in some alternate location. The hose may be configured to remove particles accumulated in sample receptacle 106 to the receptacle bag. In one embodiment, the hose may utilize gravity to transfer the particles from sample receptacle 106 to the receptacle bag without the use of a vacuum. In an alternate embodiment, a vacuum source (not shown) may be used to propel the coal particles from sample receptacle 106 into and through the hose, although this is not required. In yet another alternate embodiment, the hose may be configured to use air pressure to transfer the particles from sample receptacle 106 to the receptacle bag. In this way, the coal sample is transported from sample receptacle 106 into the receptacle bag without the use of any type of conveyor mechanism. However, it will be understood that a different style of sample receptacle could be provided, and that crushed coal could be removed from that sample retainer by a conveyor, a chute, or some other conveying means other than a hose using gravity, air pressure, or a vacuum.

As shown in FIG. 9, material sampling device 10 may be entirely suspended from and supported by a boom assembly 130 and does not require any type of tower or framework as used in existing coal samplers. FIG. 9 depicts a trailer 140, which contains an operator's cab 142 and a lift mechanism 144. Lift mechanism 144 may comprise a hydraulic lift or any other suitable device. In the illustrated version, lift mechanism 144 operates boom assembly 130, which includes a boom arm 132. Boom arm 132 may have any suitable radius of operation, including but not limited to a twenty-two foot radius (22'=6.7 m), a thirty foot radius (30'=3.05 m), or any other desired radius of operation, including a radius smaller than twenty two feet or greater than thirty feet. In this example, boom arm 132 is connected to material sampling device 10 via a two-way pivot 134. By use of this boom assembly 130 and lift mechanism 144 combination, material sampling device 10 may be readily shiftable in the vertical direction so as to be raised above a coal truck, then lowered into the load of coal within that truck. In addition, the boom arm 132 may be readily shiftable in the horizontal direction throughout its twenty-two foot (6.7 m) radius so as to accommodate different positions of coal trucks as they approach trailer 140.

It will be understood that coal sampling device 10 may be attached to a permanent structure, such as a building, rather than being installed onto a portable apparatus. In addition, material sampling device 10 may be permanently mounted onto a concrete pad.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A material sampling device comprising:
    a) an auger, wherein the auger comprises an auger blade and an auger shaft, wherein the auger is configured to extract material from a container, thereby creating a primary material sample;
    b) a first motor, wherein the auger motor is in mechanical communication with the auger shaft, wherein the first motor is configured to rotate the auger; and
    c) a rotatable tube assembly, wherein the rotatable tube assembly comprises
        i) an outer tube, wherein the outer tube is configured to house at least a portion of the auger, wherein the outer tube is configured to allow the auger to rotate within the outer tube, wherein the outer tube comprises a lower portion, wherein the lower portion is configured to rotate, wherein the outer tube further comprises an upper portion, wherein the upper portion is configured to remain stationary, and
        ii) a second motor, wherein the second motor is in mechanical communication with the lower portion of the outer tube, wherein the second motor is configured to rotate the lower portion of the outer tube.

2. The device of claim 1, wherein the outer tube further comprises a bit head, wherein the bit head is positioned on a bottom end of the lower portion of the outer tube, wherein the bit head comprises a bottom edge and at least one tooth, wherein the at least one tooth projects downward from the bottom edge, wherein the at least one tooth is configured to facilitate movement of the device through material.

3. The device of claim 2, wherein the bit head is integral with the lower portion of outer tube.

4. The device of claim 2, wherein the bit head comprises a discrete component, wherein the bit head is fixedly attached to the lower portion of the outer tube.

5. The device of claim 1, wherein the second motor is configured to produce multidirectional rotation of the lower portion of the outer tube.

6. The device of claim 1, wherein the first motor is configured to produce rotation of the auger in a first direction, wherein the second motor is configured to produce rotation of the lower portion of the outer tube in a second direction, wherein the first direction is substantially opposite the second direction, wherein the rotation of the auger in the first direction and the rotation of the lower portion of the outer tube in the second direction occur substantially simultaneously.

7. The device of claim 6, wherein the second motor is further configured to produce rotation of the lower portion of the outer tube in the first direction.

8. The device of claim 1, wherein the rotatable tube assembly further comprises:
    a) a first gear, wherein the gear is in mechanical communication with the second motor; and
    b) a turntable bearing, wherein the turntable bearing comprises a circumferential gear, wherein the circumferential gear is in mechanical communication with the first gear, wherein the turntable bearing is further in mechanical communication with the lower portion of outer tube, wherein rotation produced by the second motor is communicated to the lower portion of the outer tube via the first gear, the circumferential gear and the turntable bearing.

9. The device of claim 1, wherein the primary material sample is conveyed by the auger upward through the outer tube, wherein the outer tube further comprises an outlet through the primary material sample is moved, the device further comprising:
   a) an integral material separator, wherein the material separator is configured to separate the primary material sample received from the outlet of the outer tube, wherein the material separator comprises a first window, through which a portion of said primary material sample is directed, thereby creating a secondary material sample that automatically passes through the first window via gravity, wherein the material separator further comprises a second window in communication with a discharge shaft that is open at its bottom portion, thereby providing an opening through which the remaining portion of the primary material sample automatically passes via gravity;
   b) a material crusher, wherein the material crusher is configured to crush the secondary material sample that passes through the first window into particles small enough for useful analysis thereby creating a crushed material sample, wherein the material crusher further comprises at least one outlet; and
   c) a material collector, wherein the material collector is configured to collect the crushed material sample received from the at least one outlet of the material crusher, for analysis.

10. A coal sampling device comprising:
   a) an auger, wherein the auger comprises an auger blade and an auger shaft, wherein the auger is configured to extract coal from a container, wherein the auger is configured to rotate; and
   b) a rotatable tube assembly, wherein the rotatable tube assembly comprises an outer tube, wherein the outer tube is configured to house the auger blade and at least a portion of the auger shaft, wherein the outer tube is configured to allow the auger to rotate within the outer tube, wherein the outer tube comprises a lower portion, wherein the lower portion is configured to rotate, wherein the outer tube further comprises an upper portion, wherein the upper portion is configured to remain stationary;
      wherein the auger and the lower portion of the outer tube are configured to rotate simultaneously in opposite directions.

11. The device of claim 10, wherein the auger and the lower portion of the outer tube are further configured to rotate simultaneously in the same direction.

12. The device of claim 10, wherein the auger is configured to rotate independently of the lower portion of the outer tube, such that the auger is configured to rotate while the lower portion of the outer tube remains stationary and the lower portion of the outer tube is configured to rotate while the auger remains stationary.

13. The device of claim 10, wherein the outer tube comprises an outer surface having a length and a circumference, wherein the outer surface is substantially continuous along substantially the entire length of the outer surface, wherein the outer surface is substantially continuous across substantially the entire circumference of the outer surface.

14. The device of claim 10, wherein the outer tube further comprises an outer surface and a plurality of external features along the outer surface, wherein the external features are configured to facilitate movement of the device through the coal.

15. The device of claim 14, wherein the plurality of external features are selected from the group consisting of teeth, spirals, projections, and protuberances.

16. The device of claim 10, wherein the outer tube further comprises a bit head positioned on a bottom end of the lower portion of the outer tube, wherein the bit head further comprises an interior surface and a plurality of internal features, wherein the internal features are positioned along the interior surface of the bit head, wherein the internal features are configured to facilitate movement of the device through the coal.

17. The device of claim 16, wherein the internal features are selected from the group consisting of teeth, spirals, projections, and protuberances.

18. A method of sampling material comprising the steps of:
   a) providing a material sampling device, wherein the material sampling device comprises
      i) an auger, wherein the auger is configured to extract material from a container, wherein the auger is configured to rotate; and
      ii) a rotatable tube assembly, wherein the rotatable tube assembly comprises
         (1) an outer tube, wherein the outer tube is configured to house at least a portion of the auger, wherein the outer tube is configured to allow the auger to rotate within the outer tube, wherein the outer tube comprises
            (a) an upper portion, wherein the upper portion is configured to remain stationary, and
            (b) a lower portion, wherein the lower portion is configured to rotate;
   b) simultaneously rotating the auger in a first direction and rotating the lower portion of the outer tube in a second direction, wherein the first direction is substantially opposed to the second direction; and
   c) lowering the material sampling device into a quantity of material, wherein the auger and the lower portion of the outer tube contact the material, wherein the material sampling device penetrates into the quantity of material as the auger and the outer tube are rotating;
   d) extracting a sample of material from the quantity of material, wherein the sample is conveyed upward through the outer tube by the auger.

19. A material sampling device comprising:
   a) an auger, wherein the auger comprises an auger blade and an auger shaft;
   b) a first motor, wherein the auger motor is in mechanical communication with the auger shaft, wherein the first motor is configured to rotate the auger; and
   c) a rotatable tube assembly, wherein the rotatable tube assembly comprises
      i) an outer tube, wherein the outer tube is configured to house at least a portion of the auger, wherein the outer tube is configured to allow the auger to rotate within the outer tube, wherein the outer tube comprises a lower portion, wherein the lower portion is configured to rotate, wherein the outer tube further comprises an upper portion, wherein the upper portion is configured to remain stationary, and
      ii) a second motor, wherein the second motor is in mechanical communication with the lower portion of the outer tube, wherein the second motor is configured to rotate the lower portion of the outer tube.

* * * * *

UNITED STATES PATENT AND TRADEMARK OFFICE
CERTIFICATE OF CORRECTION

PATENT NO.        : 8,171,808 B2
APPLICATION NO.   : 12/433281
DATED             : May 8, 2012
INVENTOR(S)       : George F. Johnson, Jr. and Viktor Andreevich Zhuravlov It is certified that error appears in the above-identified patent and that said Letters Patent is hereby corrected as shown below:

Column 10, Claim 1, line 12, reads

"... wherein the auger motor is in mechanical communication ...";

which should be deleted and replaced with

"... wherein the first motor is in mechanical communication ..."

Column 12, Claim 19, line 47, reads

"... wherein the auger motor is in mechanical communication ...";

which should be deleted and replaced with

"... wherein the first motor is in mechanical communication ..."

Signed and Sealed this
Twelfth Day of March, 2013

Teresa Stanek Rea
*Acting Director of the United States Patent and Trademark Office*